US005736503A

United States Patent [19]
Vinson

[11] Patent Number: 5,736,503
[45] Date of Patent: Apr. 7, 1998

[54] HIGH SUDSING DETERGENT COMPOSITIONS WITH SPECIALLY SELECTED SOAPS

[75] Inventor: Phillip Kyle Vinson, Fairfield, Ohio

[73] Assignee: The Procter & Gamble Company, Cincinnati, Ohio

[21] Appl. No.: 774,712

[22] Filed: Jan. 3, 1997

Related U.S. Application Data

[63] Continuation of Ser. No. 466,941, Jun. 6, 1995, abandoned, which is a continuation of Ser. No. 112,164, Aug. 26, 1993, abandoned, which is a continuation-in-part of Ser. No. 984,074, Nov. 30, 1992, abandoned.

[51] Int. Cl.$^6$ .............................. C11D 3/32; C11D 17/00
[52] U.S. Cl. .................... 510/481; 510/235; 510/499; 510/501; 510/502
[58] Field of Search .......................... 510/130, 235, 510/426, 430, 481, 499, 501, 502

[56] References Cited

U.S. PATENT DOCUMENTS

| Re. 29,337 | 8/1977 | Ward | 252/108 |
|---|---|---|---|
| 1,985,424 | 12/1934 | Pigott | 260/124 |
| 2,703,798 | 3/1955 | Schwartz | 260/211 |
| 2,717,894 | 9/1955 | Schwartz | 260/211 |
| 2,965,576 | 12/1960 | Wilson | 252/137 |
| 3,226,329 | 12/1965 | MacMillan | 252/107 |
| 3,520,816 | 7/1970 | DeAcetis et al. | 252/108 |
| 3,607,761 | 9/1971 | Feighner et al. | 252/108 |
| 3,654,166 | 4/1972 | Eckert et al. | 252/117 |
| 3,734,859 | 5/1973 | Ward | 252/108 |
| 3,844,951 | 10/1974 | Fries et al. | 252/8.6 |
| 3,906,106 | 9/1975 | Jacobi | 424/312 |
| 4,704,223 | 11/1987 | Gupta et al. | 252/132 |
| 5,009,814 | 4/1991 | Kelkenberg et al. | 252/548 |
| 5,108,646 | 4/1992 | Beerse et al. | 252/174.25 |
| 5,174,927 | 12/1992 | Honsa | 252/543 |
| 5,188,769 | 2/1993 | Connor et al. | 252/548 |
| 5,254,281 | 10/1993 | Pichardo et al. | 252/108 |
| 5,269,974 | 12/1993 | Ofosu-Asante | 252/54 X |
| 5,318,728 | 6/1994 | Surutzidis et al. | 252/548 |

FOREIGN PATENT DOCUMENTS

| 59-161498 | 9/1984 | Japan | C11D 9/26 |
|---|---|---|---|
| 809060 | 5/1957 | United Kingdom . | |
| 1213333 | 9/1968 | United Kingdom . | |
| 1255309 | 4/1970 | United Kingdom . | |
| 1213333 | 11/1970 | United Kingdom | C11D 9/02 |
| 1240105 | 7/1971 | United Kingdom | C11D 9/02 |
| 1295309 | 11/1972 | United Kingdom | C11D 9/02 |
| 9213055 | 4/1972 | WIPO . | |
| 9206156 | 4/1992 | WIPO | C11D 1/65 |
| 9206157 | 4/1992 | WIPO | C11D 1/65 |
| 9213059 | 8/1992 | WIPO | C11D 9/30 |

*Primary Examiner*—Paul Lieberman
*Assistant Examiner*—Necholus Ogden
*Attorney, Agent, or Firm*—S. Robert Chuey; Ken K. Patel; Jacobus C. Rasser

[57] ABSTRACT

Detergent compositions with high sudsing properties comprise an anionic surfactant of the alkyl sulfate, alkyl ethoxy sulfate, 2-sulfonated fatty acid methyl esters, alkyl benzene sulfonates, secondary alkyl or alkenyl sulfates, alkyl ethoxy carboxylates, sulfated or polyhydroxy fatty acid amides class, and a specially selected soap such as sodium 2-butyl-1-octanoate. The compositions provide spontaneous emulsification of grease even at neutral pH, especially in the presence of calcium ions. Sudsing may optionally be boosted by incorporating magnesium ions into the compositions. Laundry and dishwashing compositions are provided. Compositions containing a polyhydroxy fatty acid amide, sulfated polyhydroxy fatty acid amide, or alkyl ethoxy carboxylate are especially useful.

7 Claims, No Drawings

5,736,503

HIGH SUDSING DETERGENT COMPOSITIONS WITH SPECIALLY SELECTED SOAPS

This is a continuation of application Ser. No. 08/466,941, filed on Jun. 6, 1995 now abandoned which is a continuation of application Ser. No. 08/112,164, filed on Aug. 26, 1993, now abandoned, which is a continuation-in-part application of U.S. patent application Ser. No. 07/984.074, filed Nov. 30, 1992, now abandoned.

FIELD OF THE INVENTION

The present invention relates to detergent compositions, especially liquid detergents, containing a specially selected soap and one or more selected anionic surfactants, and, preferably, a polyhydroxy fatty acid amide surfactant. The resulting compositions diluted in aqueous media yield extremely low interfacial tensions against greasy soils, especially in the presence of calcium ions, and are thus useful for cleaning operations. Appropriate selection of the soap provides good sudsing, and sudsing is further improved by the addition of magnesium ions. Overall, the compositions provide excellent cleaning of greasy/oily soils over a wide pH range, including the "mild" pH range of 6.5–9, and with reasonably high sudsing. Thus, the compositions are especially useful in hand dishwashing or other cleaning operations where good grease removal and high sudsing are desired by the user.

BACKGROUND OF THE INVENTION

The formulation of effective detergent compositions presents a considerable challenge. Effective compositions are required to remove a variety of soils and stains from diverse substrates. In particular, the removal of greasy/oily soils quickly and efficiently can be problematic. For example, the removal of greasy food residues from dishware in hand dishwashing operations has become a particular challenge to the formulator. Modern dishwashing compositions are, in the main, formulated as aqueous liquids; accordingly, water-stable ingredients must be used. Moreover, such compositions come into prolonged contact with skin; therefore, they must be mild. Yet, mildness is difficult to achieve in an effective dishwashing product, since products which remove grease from dishware may also tend to remove the natural skin oils from the user's hands.

Various means are employed to enhance grease and oil removal performance of detergent compositions. Grease-cutting nonionic surfactants have been employed, but some of these may be irritating to biological membranes. Attempts have been made to employ nonconventional detergent surfactants in liquid compositions. Indeed, while a review of the literature would seem to suggest that a wide selection of surfactants is available to the detergent manufacturer, the reality is that many such materials are specialty chemicals which are not suitable in low unit cost items such as home-use detergent compositions. The fact remains that most home-use detergents still comprise one or more of the conventional ethoxylated nonionic and sulfated or sulfonated anionic surfactants, presumably due to economic considerations.

The challenge to the detergent manufacturer seeking improved grease/oil removal has been increased by various environmental factors. For example, some nonbiodegradable ingredients have fallen into disfavor. Effective phosphate builders have been banned by legislation in many countries. Moreover, many surfactants are often available only from nonrenewable resources such as petrochemicals. Accordingly, the detergent formulator is quite limited in the selection of surfactants which are effective cleaners, biodegradable and, to the extent possible, available from renewable resources such as natural fats and oils, rather than petrochemicals.

Considerable attention has lately been directed to nonionic surfactants which can be prepared using mainly renewable resources, such as fatty esters and sugars. One such class of surfactants includes the polyhydroxy fatty acid amides. Moreover, the combination of such nonionic surfactants with conventional anionic surfactants such as the alkyl sulfates, alkyl benzene sulfonates, alkyl ether sulfates, and the like has also been studied. The present invention undertakes to substantially improve the grease and oil removal properties of such compositions.

Succinctly stated, the invention herein is based on the unexpected discovery that use of specially selected "soap" materials can substantially enhance the grease and oil removal properties of detergent compositions, especially, but not limited to, those which contain polyhydroxy fatty acid amides and anionic surfactants. While not intending to be limited by theory, it appears that inclusion of such soap materials into such compositions substantially enhances their ability to rapidly lower the interfacial tension of aqueous washing liquors with greasy and oily soils. This substantial reduction of interfacial tension leads to what might be termed "spontaneous emulsification" of greasy and oily soils, thereby speeding their removal from soiled surfaces and inhibiting the redeposition of the soils onto substrates. This phenomenon is particularly noteworthy in the case of hand dishwashing operations with greasy dishware.

It has further been determined that the use of common linear soaps does not provide optimum high sudsing, as is desired by the users of such compositions especially for hand dishwashing purposes. Indeed, linear soaps are often conventionally used to diminish suds levels in certain European fabric laundering detergents. The consumer tends to equate performance of dishwashing products with suds height and volume, and even uses the diminution of suds to signal the need for the addition of more product into the dishwash bath. Accordingly, the use of conventional linear soaps in such compositions is sub-optimal, inasmuch as sudsing can suffer. Moreover, some soaps tend to provide their best grease cutting performance at pH's in the alkaline range, whereas it is much more desirable to have dishwashing compositions formulated at near-neutrality.

By the present invention it has been determined that certain soaps, e.g., secondary alkyl carboxyls, not only provide the desired lowering of interfacial tension, with its attendant increase in grease removal performance, but also allow the formulation of reasonably high sudsing liquid compositions which are stable and homogeneous. It has further been discovered that the inclusion of calcium ions in such compositions still further enhances the lowered interfacial tension phenomenon, and thus still further enhances grease removal performance. It has further been discovered that the sudsing of such compositions can be increased even further by the addition of magnesium ions. It has further been discovered that these special benefits can be achieved at neutral pH, which enhances mildness and avoids the need for costly buffering chemicals. It has yet further been discovered that certain secondary alkyl carboxyls are preferred for product odor and/or control of the viscosity of fully formulated detergent products. The overall unexpected improvements in performance and aesthetic qualities, especially sudsing, provide the basis for the present invention, which is described in more detail hereinafter.

BACKGROUND ART

A method for preparing crude polyhydroxy fatty acid amides (glucamides) is described in U.S. Pat. No. 1,985,424, Piggott, and in U.S. Pat. No. 2,703,798, Schwartz. The use of such glucamides with various synthetic anionic surfactants is described in U.S. Pat. No. 2,965,576, corresponding to G.B. Patent 809,060. The sulfuric esters of acylated glucamines are disclosed in U.S. Pat. No. 2,717,894, Schwartz.

SUMMARY OF THE INVENTION

The present invention encompasses high sudsing detergent compositions which comprise an anionic surfactant which is a member selected from the group consisting of primary alkyl and alkenyl sulfates (AS), α-sulfonated fatty acid methyl esters (MES), alkyl benzene sulfonates (LAS), alkyl ethoxy sulfates (AES), alkyl ethoxy carboxylates (AEC), sulfated polyhydroxy fatty acid amides (SPFA), and secondary alkyl or alkenyl sulfates (SAS), and mixtures thereof, and a specially selected soap (as defined hereinafter), and, optionally, one or more nonionic surfactants. Typically the weight ratio of anionic:soap is from about 30:1 to about 2:1, preferably from 9:1 to 3:1.

The invention also encompasses an improved method for providing high sudsing compositions which comprise one or more conventional anionic surfactants, nonionic surfactants, or mixtures thereof and a conventional linear soap, said method consisting of replacing said linear soap in said composition with a specially selected soap, as disclosed hereinafter. By means of said method, extremely low interfacial tensions and spontaneous grease/oil emulsificaton are secured with concurrent high sudsing.

A preferred detergent composition according to this invention is illustrated by a mixed nonionic/anionic/special secondary soap surfactant system which comprises:

(a) a polyhydroxy fatty acid amide of the formula

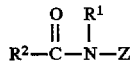

(I)

wherein $R^1$ is H, $C_1$–$C_8$ hydrocarbyl (preferably methyl), 2-hydroxyethyl, 2-hydroxypropyl, or a mixture therein, $R^2$ is $C_5$–$C_{32}$ hydrocarbyl, a Z is a polyhydroxyhydrocarbyl moiety having a linear hydrocarbyl chain with at least two hydroxyls directly connected to the chain; and (b) an anionic surfactant which is a member selected from the group consisting of AS, AES, LAS, MES, SPFA, AEC and SAS, and mixtures thereof; at a weight ratio of (a):(b) of from about 20:1 to about 1:10; and (c) a special secondary $C_{12}$–$C_{13}$ soap.

Preferred compositions herein comprise at least about 10%, preferably from about 25% to about 65%, by weight of said mixed anionic/nonionic/soap surfactant system.

The specially selected soaps typically comprise at least about 1% by weight of the compositions herein and preferably comprise from about 3% to about 15% by weight of the compositions. Stated otherwise, the weight ratio of selected soap, preferably secondary soap (c) to the combined mixture of nonionic/anionic (a+b) is in the range from about 1:30 to about 1:2, preferably about 1:9 to about 1:3.

Other compositions herein will also contain from about 2% to about 40% by weight of an additional detersive surfactant, especially the nonionic surfactants such as the $C_6$–$C_{24}$ alkoxylated alcohols or alkoxylated $C_6$–$C_{24}$ alkyl phenols. The invention thus encompasses compositions which comprise from about 10% to about 65% by weight of said mixed nonionic/anionic/soap surfactant system, from about 2% to about 40% by weight of an ethoxylated $C_6$–$C_{24}$, preferably $C_8$–$C_{14}$, alcohol or alkyl phenol, and optional builders and detersive enzymes.

The invention also encompasses high sudsing methods for removing greasy/oily stains and soils from items such as tableware, cooking utensils, glassware, dishes and the like, comprising contacting such items thus soiled with an aqueous bath containing at least about 0.02% by weight of a composition which comprises a mixed nonionic/anionic/special selected soap, preferably secondary soap surfactant system, especially one which comprises:

(a) a nonionic surfactant which is a polyhydroxy fatty acid amide as noted above wherein $R^1$ is preferably methyl;

(b) an anionic surfactant which is a member selected from the group consisting of AS, AES, LAS, SAS, SPFA, AEC and MES;

at a weight ratio of (a):(b) of from about 10:1 to about 1:10;

(c) specially selected $C_{10}$–$C_{16}$, preferably $C_{12}$–$C_{13}$, secondary soap;

(d) optionally, a source of calcium ions, magnesium ions, or both; and (e) optionally, an ethoxylated (EO 6–12) $C_8$–$C_{14}$ alcohol.

As disclosed herein, the present compositions can contain a source of calcium ions, which enhances grease removal performance and/or a source of magnesium ions, which further enhances sudsing. Such compositions will typically contain at least about 0.05% by weight of calcium ions and, optionally, a suds boosting amount of magnesium ions, generally at least about 0.05%.

All percentages, ratios and proportions herein are by weight, unless otherwise specified. All documents cited are incorporated herein by reference.

DETAILED DESCRIPTION OF THE INVENTION

"SPECIALLY SELECTED SECONDARY SOAPS"

The term "specially selected soaps" (aka "alkyl carboxyl surfactants") herein does not encompass the classic, conventional water-soluble salts of $C_{10}$–$C_{18}$ linear saturated and unsaturated fatty acids, since these classic soaps tend to reduce sudsing. It has now been discovered that, for high sudsing compositions such as dishwashing liquids, the specially selected soaps, as defined hereinafter, are much preferred. Compositions according to the present invention containing such water-soluble special soaps exhibit quite low interfacial tensions, good grease removal properties and high sudsing, even at pH's near neutrality, i.e., in the range of ca. 6.5–9.0. As a general proposition, the improved qualities of the compositions herein appear to peak with such special soaps which are about $C_{12}$–$C_{13}$, and decrease somewhat with special soaps which contain more than about 14 carbon atoms or less than about 11 carbon atoms, especially with respect to spontaneous emulsification of greasy soils. Accordingly, the $C_{12}$–$C_{13}$ special soaps are preferred herein. (The aforesaid C numbers are intended to include the total carbon number including the carboxylate carbon atom in the special soaps.) These soaps can be employed in any water-soluble salt form, e.g., alkali metal, alkaline earth metals ammonium, alkanolammonium, dialkanol ammonium, trialkanol ammonium, 1–5 carbon alkyl substituted ammonium, basic amino acid groups, and the like; all of these counterions are well-known to manufacturers. The sodium salt form is convenient, cheap and effective. The acid form can also be used, but will usually be converted into the ionic form by pH adjustments which are made during processing of the compositions.

The specially selected secondary soaps employed herein to provide low interfacial tension, spontaneous emulsification of grease and yet allow for reasonably high sudsing are those which contain a carboxyl unit connected to a secondary carbon. It is to be understood herein that the secondary carbon can be in a ring structure, e.g., as in p-octyl benzoic acid, or as in alkyl-substituted cyclohexyl carboxylates. The special soaps should contain no ether linkages, no ester linkages and no hydroxyl groups. There should be no nitrogen atoms in the head-group (amphiphilic portion). The special soaps usually contain 11–14 total carbon atoms, although slightly more (e.g., about 14–16) are preferred if the soap contains a ring structure, as noted above, e.g., p-octyl benzoic acid.

For purposes of illustration, and not by way of limitation, the special soaps based on the following secondary fatty acids produce low interfacial tension and spontaneous emulsification when used in the manner of this invention: 2-methyl-1-undecanoic acid; 2-ethyl-1-decanoic acid; 2-propyl-1-nonanoic acid; 2-butyl-1-octanoic acid; 2-pentyl-1-heptanoic acid; 2-methyl-1-dodecanoic acid; 2-ethyl-1-undecanoic acid; 2-propyl-1-decanoic acid; 2-butyl-1-nonanoic acid; 2-pentyl-1-octanoic acid; p-octyl benzoic acid; and trans-4-pentylcyclohexane carboxylic acid. By contrast, and to illustrate the importance of α-carbon substitution, chain length, and the like, the following carboxyls do not provide the desirable spontaneous emulsification effect herein: p-nonyloxy benzoic acid; 2-heptyl undecanoic acid; 12-hydroxy dodecanoic acid; and 2-hydroxy lauric acid.

The following general structures further illustrate some of the special soaps (or their precursor acids) employed in this invention.

A. A highly preferred class of soaps used herein comprises the $C_{10}$–$C_{16}$ secondary carboxyl materials of the formula $R^3$CH($R^4$)COOM, wherein $R^3$ is $CH_3(CH_2)_x$ and $R^4$ is $CH_3(CH_2)_y$, wherein y can be 0 or an integer from 1 to 6, x is an integer from 6 to 12 and the sum of (x+y) is 6–12, preferably 7–11, most preferably 8–9.

B. Another class of special soaps useful herein comprises those carboxyl compounds wherein the carboxyl substituent is on a ring hydrocarbyl unit, i.e., secondary soaps of the formula $R^5$–$R^6$-COOM, wherein $R^5$ is $C_7$–$C_{10}$, preferably $C_8$–$C_9$, alkyl or alkenyl and $R^6$ is a ring structure, such as benzene, cyclopentane, cyclohexane, and the like. (Note: $R^5$ can be in the ortho, meta or para position relative to the carboxyl on the ring.)

C. Still another class of soaps includes the $C_{10}$–$C_{18}$ primary and secondary carboxyl compounds of the formula $R^7$CH($R^8$)COOM, wherein the sum of the carbons in $R^7$ and $R^8$ is 8–16, $R^7$ is of the form $CH_3$-$(CHR^9)_x$ and $R^8$ is of the form H-$(CHR^9)_y$, where x and y are integers in the range 0–15 and $R^9$ is H or a $C_{1-4}$ linear or branched alkyl group. $R^9$ can be any combination of H and $C_{1-4}$ linear or branched alkyl group members within a single —$(CHR^9)_{x,y}$ group; however, each molecule in this class must contain at least one $R^9$ that is not H. These types of molecules can be made by numerous methods, e.g. by hydroformylation and oxidation of branched olefins, hydroxycarboxylation of branched olefins, oxidation of the products of Guerbet reaction involving branched oxoalcohols. The branched olefins can be derived by oligomerization of shorter olefins, e.g. butene, isobutylene, branched hexene, propylene and pentene.

D. Yet another class of soaps includes the $C_{10}$–$C_{18}$ tertiary carboxyl compounds, e.g., neo-acids, of the formula $R^{10}$C$R^{11}$($R^{12}$)COOM, wherein the sum of the carbons in $R^{10}$, $R^{11}$ and $R^{12}$ is 8–16. $R^{10}$, $R^{11}$, and $R^{12}$ are of the form $CH_3$—$(CHR^{13})_x$, where x is an integer in the range 0–13, and $R^{13}$ is H or a $C_{1-4}$ linear or branched alkyl group. Note that $R^{13}$ can be any combination of H and $C_{1-4}$ linear or branched alkyl group members within a single —$(CHR^{13})_x$ group. These types of molecules result from addition of a carboxyl group to a branched olefin, e.g., by the Koch reaction. Commercial examples include the neodecanoic acid manufactured by Exxon, and the Versatic™ acids manufactured by Shell.

In each of the above formulas A, B, C and D, the species M can be any suitable, especially water-solubilizing, counterion, e.g., H, alkali metal, alkaline earth metal, ammonium, alkanolammonium, di- and tri-alkanolammonium, $C_1$–$C_5$ alkyl substituted ammonium and the like. Sodium is convenient, as is diethanolammonium.

Formula C class soaps comprise secondary carboxyl compounds of the formula $CH_3(CHR)_k$—$(CH_2)_m$—$(CHR)_n$—$CH(COOM)(CHR)_o$—$(CH_2)_p$—$(CHR)_q$—$CH_3$, wherein each R is $C_1$–$C_4$ alkyl, wherein k, n, o, q are integers in the range of 0–2 and m and p are integers in the range of 0–8, provided that the total number of carbon atoms (including the carboxylate) is in the range of 10 to 18.

Preferred secondary soaps for use herein are water-soluble members selected from the group consisting of the water-soluble salts of 2-methyl-1-undecanoic acid, 2-ethyl-1-decanoic acid, 2-propyl-1-nonanoic acid, 2-butyl-1-octanoic acid; 2-pentyl-1-heptanoic acid; 2-methyl-1-dodecanoic acid; 2-ethyl-1-undecanoic acid; 2-propyl-1-decanoic acid; 2-butyl-1-nonanoic acid; 2-pentyl-1-octanoic acid and mixtures thereof.

In a preferred embodiment the secondary soap is selected on the basis of product odor both in neat form and dilute aqueous solutions. Secondary soaps of the form $R^3$CH($R^4$)COOM in which the total carbon number is constant, odor improves as the length of the shorter alkyl chain ($R^4$) increases, e.g. 2-butyl-1-octanoic acid is preferred over 2-methyl-1-undecanoic acid. Similarly, secondary soaps in which $R^4$ is a fixed carbon number, the odor improves as the total carbon increases (i.e. $R^3$ increases). For example, 2-methyl-1-dodecanoic acid is preferred over 2-methyl-1-undecanoic acid.

Secondary soaps can also be selected for their viscosity effect on the fully formulated product. For example, secondary soaps of the form $R^3$CH($R^4$)COOM in which the total carbon number is constant, the product viscosity decreases as $R^4$ carbon number increases. For example, 2-butyl-1-octanoic acid produces a lower viscosity than 2-methyl-1-undecanoic acid. If $R^4$ is constant, the viscosity increases with an increase in total carbon number. Thus, 2-methyl-1-dodecanoic would yield a higher product viscosity than 2-methyl-1-undecanoic acid.

CALCIUM AND MAGNESIUM SOURCE

The preferred compositions herein will also contain from about 0% to about 3%, preferably from about 0% to about 1%, by weight, of calcium ions. High sudsing compositions will contain from about 0% to about 3%, preferably from about 0% to about 1%, by weight of magnesium ions. Sources of calcium and magnesium can be any convenient water-soluble and toxicologically acceptable salt, including but not limited to, $CaCl_2$, $MgCl_2$, $Ca(OH)_2$, $Mg(OH)_2$, $CaBr_2$, $MgBr_2$, $MgSO_4$, $CaSO_4$, Ca formate, Ca malate, Mg malate; Ca maleate, Mg maleate, or the calcium and/or magnesium salts of anionic surfactants or hydrotropes. $CaCl_2$ and $MgCl_2$ are convenient and preferred herein.

SUDSING

The sudsing qualities of the compositions herein can be tested by any means which mimics realistic in-use situations. For example, the formulator can employ a manual dishwashing test such as the SM-1 Shell test method. This is a practical method which determines the average number of soiled plates which can be manually washed under controlled conditions until the foam collapses.

In a representative type of testing, dinner plates are soiled with mixed foodstuffs. Each plate is then washed separately in an aqueous bath containing the compositions of the present invention, using a controlled number of agitations per plate. The number of plates so washed are counted until the suds have substantially disappeared.

A comparison of the number of plates washed with a control test using any desired hand dishwashing composition can be made to assess the equivalency of sudsing.

In this type of testing, the suds properties of the present compositions are judged to be up to about 80-90% equivalent to those of high-sudsing, commercial hand dishwashing detergents. By contrast, compositions using straight-chain fatty acids such as lauric acid have sudsing levels only about 30%-40% that of such commercial detergents. As noted hereinafter, if additional suds boosters are added to the present compositions, sudsing levels as high as 90%-100% that of even premium commercial liquid dishwashing detergents may be achieved.

INTERFACIAL TENSION

By "interfacial tension" ("IFT") herein is meant the tension measured at the oil/water interface. IFT measurements using the spinning drop technique, are disclosed by Cayias, Schechter and. Wade, "The Measurement of Low Interfacial Tension via the Spinning Drop Technique", ACS Symposium Series No. 8 (1975) ADSORPTION AT INTERFACES, beginning at page 234. Equipment for running IFT measurements is currently available from W. H. Wade, Depts. of Chemistry and Chemical Engineering, The University of Texas at Austin, Austin, Tex. 78712.

By "low interfacial tension" herein is meant an IFT which is sufficiently low that "spontaneous emulsification", i.e., rapid emulsification with little or no mechanical agitation, can occur. For example, using a typical fatty acid N-methyl glucamide nonionic surfactant, at concentrations in water ranging from about 300 ppm to about 600 ppm and at water hardness ($Ca^{++}$) concentrations of 2 grains/gallon (14 ppm), 7 gr/gal (48 ppm) and 15 gr/gal (103 ppm) one notes a range of IFT from about 0.25 dynes/cm to about 0.4 dynes/cm. Under such conditions, "spontaneous emulsification" of grease/oil soil, if any, is minimal.

By contrast, when the aforesaid nonionic surfactant is employed with a specially selected soap at a nonionic:soap ratio of 410:90, the IFT is reduced to 0.15 dynes/cm, or less, and spontaneous oil emulsification is noted.

SPONTANEOUS EMULSIFICATION

The "spontaneous emulsification" of greasy/oily soils provided by the compositions herein can be simply, but convincingly, demonstrated by admixing a detergent composition in accordance with the invention containing the specially selected soap with water. After dissolution of the detergent, a few drops of oil to which a colored oil-soluble dye has been added are added to the detergent solution. With minimal agitation, the entire system appears to take on the color of the dye, due to the dyed oil having been finely dispersed by the spontaneous emulsification effect. This dispersion remains for a considerable length of time, typically 30 minutes to several hours, even when agitation has stopped. By contrast, with surfactant systems which fail to provide spontaneous emulsification, the dyed oil droplets produced during agitation rapidly coalesce to form one or more relatively large oil globules at the air/water interface.

More specifically, this demonstration of spontaneous emulsification can be run as follows.

A consumer relevant test soil is dyed with 0.5% Oil Red EGN. A 100 ml sample of the detergent composition being tested is prepared at the desired concentration (typically, about 500 ppm) and temperature in water which is "prehardened" to any desired concentration of calcium ions (typically, about 48 ppm), and contained in an 8 oz. capped jar. The sample pH is adjusted to the intended end-use pH (typically in the range of 6.5 to 8) and 0.2 g of the test soil is added. The jar is shaken 4 times and the sample graded. Alternatively, the sample is placed in a beaker and stirred with a stir bar for 15 seconds. The sample is graded as follows:

0=Clear solution with large red oil droplets in it (0.1–5 mm diameter), i.e., no emulsification;

1=Solution has a definite pink appearance with red oil droplets in it (0.1–1 mm), i.e., slight emulsification;

2=Solution is dark pink with small red droplets in it, i.e., moderate emulsification;

3=Solution is red with small red droplets in it (1–200 μm), i.e., emulsification is substantial;

4=Solution is dark red with little or no visible droplets (<1–50 μm), i.e., emulsification is complete.

Note: The grading can also be done spectrophotometrically (based on light transmittance).

DETERSIVE SURFACTANTS

The compositions herein will comprise from about 3% to about 40% by weight of anionic surfactants. Nonlimiting examples of surfactants useful herein include the conventional $C_{11}$–$C_{16}$ alkyl benzene sulfonates, the $C_{12}$–$C_{18}$ primary and secondary alkyl sulfates and $C_{12}$–$C_{18}$ unsaturated (alkenyl) sulfates such as oleyl sulfate, the $C_{10}$–$C_{18}$ alkyl ethoxy sulfates, the $C_{10}$–$C_{18}$ alkyl polyglycosides and their corresponding sulfated polyglycosides, $C_{12}$–$C_{18}$ alkyl methyl ester sulfonates (α-sulfonated fatty acid methyl esters), the $C_{10}$–$C_{18}$ alkyl ethoxy carboxylates, $C_8$–$C_{14}$ alkyl ethoxylates (EO 6–12) and alkyl phenol ethoxylates, and $C_{10}$–$C_{18}$ amine oxides. The $C_{10}$–$C_{18}$ alkyl ethoxy (EO average 1–5, preferably EO [avg.] 1–3) sulfates are especially preferred in high sudsing hand dishwashing compositions. The $C_{10}$–$C_{18}$ betaines and sulfobetaines (aka "sultaines") are also high sudsing, mild surfactants for such use, especially in combination with the alkyl ethoxy sulfates.

Special attention is warranted with respect to the class of anionic surfactants which comprise the sulfated analogs of the polyhydroxy fatty acid amides nonionic surfactant of formula (I). (These sulfated materials can be prepared in the manner of Schwartz U.S. Pat. No. 2,717,894, cited above, or by the reaction of a $SO_3$:pyridine complex with a compound of formula [I]. Such materials may be mono- or polysulfated on one or more of their hydroxy groups; monosulfated is preferred.) Such anionics, especially sulfated $C_{10}$–$C_{18}$ N-methyl glucamide, have a strong synergy with the special soaps to lower IFT's and to provide spontaneous emulsification.

Special attention is also warranted with respect to the alkyl ethoxy carboxylates of the formula R—(OCH$_2$CH$_2$)$_x$OCH$_2$C(O)OM, wherein R is typically $C_8$–$C_{18}$ and x is 0 to 6. Such anionics also have a strong synergy with the special soaps to lower IFT's and to provide spontaneous emulsification.

In view of the foregoing, highly preferred compositions herein comprise: (i) a member selected from the group consisting of the sulfated polyhydroxy fatty acid amides and the alkyl ethoxy carboxylates; and (ii) a secondary soap which is a member selected from the group consisting of the acids or water-soluble salts of 2-methyl-1-undecanoic acid, 2-ethyl-1-decanoic acid, 2-propyl-1-nonanoic acid, 2-butyl-1-octanoic acid, 2-pentyl-1-heptanoic acid, 2-methyl-1-dodecanoic acid, 2-ethyl-1-undecanoic acid; 2-propyl-1-decanoic acid; 2-butyl-1-nonanoic acid; and 2-pentyl-1-octanoic acid; preferably at a weight ratio of (i) to (ii) in the range of 1:1 to 5:1. Such mixtures of components (i) and (ii) can be used alone or in combination with conventional nonionic surfactants or polyhydroxy fatty acid amide nonionics.

In addition to the specially selected secondary soaps and the aforesaid detersive surfactants, the compositions and processes of this invention most preferably also contain high quality polyhydroxy fatty acid amide surfactants which are substantially free of cyclized and ester-amide by-products. Such nonionics have a strong synergy with the special soaps to lower IFT's and to provide spontaneous emulsification. For high sudsing compositions, especially hand-wash, most especially hand dishwashing where the consumer expects high, persistent suds, the polyhydroxy fatty acid amides preferably should also be substantially free of contamination by residual sources of classical fatty acids. The present invention thus encompasses mixtures of such polyhydroxy fatty acid amides and secondary soaps at a weight ratio of 1:10 to 10:1, preferably 1:5 to 5:1.

While polyhydroxy fatty acid amides can be made by the process of Schwartz, above, contamination with cyclized by-products and other colored materials can be problematic. As an overall proposition, the preparative methods described in WO-9,206,154 and WO-9,206,984 will afford high quality polyhydroxy fatty acid amides. The methods comprise reacting N-alkylamino polyols with, preferably, fatty acid methyl esters in a solvent using an alkoxide catalyst at temperatures of about 85° C. to provide high yields (90–98%) of polyhydroxy fatty acid amides having desirable low levels (typically, less than about 1.0%) of sub-optimally degradable cyclized by-products and also with improved color and improved color stability, e.g., Gardner Colors below about 4, preferably between 0 and 2. (With compounds such as butyl, iso-butyl and n-hexyl, the methanol introduced via the catalyst or generated during the reaction provides sufficient fluidization that the use of additional reaction solvent may be optional.) For the preferred high sudsing compositions herein, the N-methyl and N-hydroxyalkyl amine compounds are most preferred. If desired, any unreacted N-alkylamino polyol remaining in the product can be acylated with an acid anhydride, e.g., acetic anhydride, maleic anhydride, or the like, to minimize the overall level of amines in the product. Residual sources of classical fatty acids, which can suppress suds, can be depleted by reaction with, for example, triethanolamine.

By "cyclized by-products" herein is meant the undesirable reaction by-products of the primary reaction wherein it appears that the multiple hydroxyl groups in the polyhydroxy fatty acid amides can form ring structures which are, in the main, not readily biodegradable. It will be appreciated by those skilled in the chemical arts that the preparation of the polyhydroxy fatty acid amides herein using the di- and higher saccharides such as maltose will result in the formation of polyhydroxy fatty acid amides wherein linear substituent Z (which contains multiple hydroxy substituents) is naturally "capped" by a polyhydroxy ring structure. Such materials are not cyclized by-products, as defined herein.

More generally, the compositions and processes herein preferably employ polyhydroxy fatty acid amide surfactants of the formula:

wherein: $R^1$ is H, $C_1$–$C_8$ hydrocarbyl, 2-hydroxyethyl, 2-hydroxypropyl, or a mixture thereof, preferably $C_1$–$C_4$ alkyl, more preferably $C_1$ or $C_2$ alkyl, most preferably $C_1$ alkyl (i.e., methyl); and $R^2$ is a $C_5$–$C_{32}$ hydrocarbyl moiety, preferably straight chain $C_7$–$C_{19}$ alkyl or alkenyl, more preferably straight chain $C_9$–$C_{17}$ alkyl or alkenyl, most preferably straight chain $C_{11}$–$C_{19}$ alkyl or alkenyl, or mixture thereof; and Z is a polyhydroxyhydrocarbyl moiety having a linear hydrocarbyl chain with at least 2 (in the case of glyceraldehyde) or at least 3 hydroxyls (in the case of other reducing sugars) directly connected to the chain, or an alkoxylated derivative (preferably ethoxylated or propoxylated) thereof. Z preferably will be derived from a reducing sugar in a reductive amination reaction; more preferably Z is a glycityl moiety. Suitable reducing sugars include glucose, fructose, maltose, lactose, galactose, mannose, and xylose, as well as glyceraldehyde. As raw materials, high dextrose corn syrup, high fructose corn syrup, and high maltose corn syrup can be utilized as well as the individual sugars listed above. These corn syrups may yield a mix of sugar components for Z. It should be understood that it is by no means intended to exclude other suitable raw materials. Z preferably will be selected from the group consisting of —CH$_2$—(CHOH)$_n$—CH$_2$OH, —CH(CH$_2$OH)—(CHOH)$_{n-1}$—CH$_2$OH, —CH$_2$—(CHOH)$_2$(CHOR')(CHOH)—CH$_2$OH, where n is an integer from 1 to 5, inclusive, and R' is H or a cyclic mono- or polysaccharide, and alkoxylated derivatives thereof. Most preferred are glycityls wherein n is 4, particularly —CH$_2$—(CHOH)$_4$—CH$_2$OH.

In Formula (I), $R^1$ can be, for example, N-methyl, N-ethyl, N-propyl, N-isopropyl, N-butyl, N-isobutyl, N-2-hydroxy ethyl, or N-2-hydroxy propyl. For highest sudsing, $R^1$ is preferably methyl or hydroxyalkyl.

$R^2$-CO-N< can be, for example, cocamide, stearamide, oleamide, lauramide, myristamide, capricamide, palmitamide, tallowamide, etc.

Z can be 1-deoxyglucityl, 2-deoxyfructityl, 1-deoxyxylityl, 1-deoxymaltityl, 1-deoxylactityl, 1-deoxygalactityl, 1-deoxymannityl, 1-deoxymaltotriotityl, 2,3-dihydroxypropyl (from glyceraldehyde), etc.

SUDS BOOSTERS

In addition to the foregoing, the sudsing of the instant compositions can be further increased by the inclusion of suds boosters such as the coconut alkyl ($C_{12}$–$C_{14}$) and $C_{16}$–$C_{18}$ fatty acid alkanolamides in the compositions. Preferred boosters herein include $C_{10-16}$ monoethanol amide, $C_{10-16}$ DEA, $C_{10-16}$ amine oxide, $C_{10-16}$ amidopropyl amine oxide, $C_{10}$–$C_{16}$ sulfobetaines and $C_{10}$–$C_{16}$ betaines. Suds boosters are typically used at levels of from about 1% to about 10% by weight of the finished detergent compositions.

ADJUNCT INGREDIENTS

The aforesaid surfactant/selected soap mixtures can also be used with conventional "detersive adjunct" materials to provide a wide variety of fully-formulated detergent compositions. The "detersive adjunct" materials will vary, depending on the intended end-use of the final compositions. Besides high sudsing dishwashing compositions, high sudsing fabric washing compositions (especially hand-washing of fabrics, where high sudsing is appreciated by the consumer), hair shampoos and the like are typical, non-limiting examples of such compositions. The following are intended only to be illustrations of such adjuncts, more examples of which will readily come to mind of the skilled formulator.

Enzymes—Detersive enzymes can optionally be included in the detergent formulations for a wide variety of purposes, especially for fabric laundering, including removal of protein-based, carbohydrate-based, or triglyceride-based stains, for example, and prevention of refugee dye transfer. The enzymes to be incorporated include proteases, amylases, lipases, cellulases, and peroxidases, as well as mixtures thereof. Other types of enzymes may also be included. They may be of any suitable origin, such as vegetable, animal, bacterial, fungal and yeast origin. However, their choice is governed by several factors such as pH-activity and/or stability optima, thermostability, stability versus active detergents, builders and so on. In this respect bacterial or fungal enzymes are preferred, such as bacterial amylases and proteases, and fungal cellulases.

Enzymes are normally incorporated at levels sufficient to provide up to about 5 mg by weight, more typically about 0.05 mg to about 3 mg, of active enzyme per gram of the composition.

Suitable examples of proteases are the subtilisins which are obtained from particular strains of *B.subtilis* and *B.licheniforms*. Another suitable protease is obtained from a strain of Bacillus, having maximum activity throughout the pH range of 8–12, developed and sold by Novo Industries A/S under the registered trade name ESPERASE. The preparation of this enzyme and analogous enzymes is described in British Patent Specification No. 1,243,784 of Novo. Proteolytic enzymes suitable for removing protein-based stains that are commercially available include those sold under the tradenames ALCALASE and SAVINASE by Novo Industries A/S (Denmark) and MAXATASE by International Bio-Synthetics, Inc. (The Netherlands). Other proteases include Protease A (see European Patent Application 130,756, published Jan. 9, 1985) and Protease B (see European Patent Application Serial No. 87303761.8, filed Apr. 28, 1987, and European Patent Application 130,756, Bott et al, published Jan. 9, 1985).

Amylases include, for example, α-amylases described in British Patent Specification No. 1,296,839 (Novo), RAPIDASE, International Bio-Synthetics, Inc. and TERMAMYL, Novo Industries.

The cellulases usable in the present invention include both bacterial or fungal cellulase. Preferably, they will have a pH optimum of between 5 and 9.5. Suitable cellulases are disclosed in U.S. Pat. No. 4,435,307, Barbesgoard et al, issued Mar. 6, 1984, which discloses fungal cellulase produced from Humicola insolens and Humicola strain DSM1800 or a cellulase 212-producing fungus belonging to the genus Aeromonas, and cellulase extracted from the hepatopancreas of a marine mollusk (Dolabella Auricula Solander). Suitable cellulases are also disclosed in GB-A-2.075.028; GB-A-2.095.275 and DE-OS-2.247.832.

Suitable lipase enzymes for detergent usage include those produced by microorganisms of the Pseudomonas group, such as Pseudomonas stutzeri ATCC 19.154, as disclosed in British Patent 1,372,034. See also lipases in Japanese Patent Application 53-20487, laid open to public inspection on Feb. 24, 1978. This lipase is available from Amano Pharmaceutical Co. Ltd., Nagoya, Japan, under the trade name Lipase P "Amano," hereinafter referred to as "Amano-P." Other commercial lipases include Amano-CES, lipases ex *Chromobacter viscosum*, e.g. *Chromobacter viscosum* var. *lipolyticum* NRRLB 3673, commercially available from Toyo Jozo Co., Tagata, Japan; and further *Chromobacter viscosum* lipases from U.S. Biochemical Corp., U.S.A. and Disoynth Co., The Netherlands, and lipases ex *Pseudomonas gladioli*.

Peroxidase enzymes are used in combination with oxygen sources, e.g., percarbonate, perborate, persulfate, hydrogen peroxide, etc. They are used for "solution bleaching," i.e. to prevent transfer of dyes or pigments removed from substrates during wash operations to other substrates in the wash solution. Peroxidase enzymes are known in the art, and include, for example, horseradish peroxidase, ligninase, and haloperoxidase such as chloro- and bromo-peroxidase. Peroxidase-containing detergent compositions are disclosed, for example, in PCT International Application WO 89/099813, published Oct. 19, 1989, by O. Kirk, assigned to Novo Industries A/S.

A wide range of enzyme materials and means for their incorporation into synthetic detergent granules is also disclosed in U.S. Pat. No. 3,553,139, issued Jan. 5, 1971 to McCarty et al (). Enzymes are further disclosed in U.S. Pat. No. 4,101,457, Place et al, issued Jul. 18, 1978, and in U.S. Pat. No. 4,507,219, Hughes, issued Mar. 26, 1985, both. Enzyme materials useful for liquid detergent formulations, and their incorporation into such formulations, are disclosed in U.S. Pat. No. 4,261,868, Hora et al, issued Apr. 14, 1981. Enzymes for use in detergents can be stabilized by various techniques. Enzyme stabilization techniques are disclosed and exemplified in U.S. Pat. No. 4,261,868, issued Apr. 14, 1981 to Horn, et al, U.S. Pat. No. 3,600,319, issued Aug. 17, 1971 to Gedge, et al, and European Patent Application Publication No. 0 199 405, Application No. 86200586.5, published Oct. 29, 1986, Venegas. Enzyme stabilization systems are also described, for example, in U.S. Pat. Nos. 4,261,868, 3,600,319, and 3,519,570.

Optional Ingredients—In addition to enzymes, the compositions herein can optionally include one or more other detergent adjunct materials or other materials for assisting or enhancing cleaning performance, treatment of the substrate to be cleaned, or to modify the aesthetics of the detergent composition (e.g., perfumes, colorants, dyes, etc.).

Builders—Detergent builders can optionally be included in the compositions herein to assist in controlling mineral hardness. Inorganic as well as organic builders can be used. Builders are typically used in fabric laundering compositions to assist in the removal of particulate soils.

The level of builder can vary widely depending upon the end use of the composition and its desired physical form. When present, the compositions will typically comprise at least about 1% builder. Liquid formulations typically comprise from about 5% to about 50%, more typically about 5% to about 30%, by weight, of detergent builder. Granular formulations typically comprise from about 10% to about 80%, more typically from about 15% to about 50% by weight, of the detergent builder. Lower or higher levels of builder, however, are not meant to be excluded.

Inorganic detergent builders include, but are not limited to, the alkali metal, ammonium and alkanolammonium salts of polyphosphates (exemplified by the tripolyphosphates, pyrophosphates, and glassy polymeric meta-phosphates), phosphonates, phytic acid, silicates, carbonates (including bicarbonates and sesquicarbonates), sulphates, and aluminosilicates. However, non-phosphate builders are required in some locales. Importantly, the compositions herein function surprisingly well even in the presence of the so-called "weak" builders (as compared with phosphates) such as citrate, or in the so-called "underbuilt" situation that may occur with zeolite or layered silicate builders.

Examples of silicate builders are the alkali metal silicates, particularly those having a $SiO_2:Na_2O$ ratio in the range 1.6:1 to 3.2:1 and layered silicates, such as the layered sodium silicates described in U.S. Pat. No. 4,664,839, issued May 12, 1987 to H. P. Rieck. However, other silicates may also be useful such as for example magnesium silicate, which can serve as a crispening agent in granular formulations, as a stabilizing agent for oxygen bleaches, and as a component of suds control systems.

Examples of carbonate builders are the alkaline earth and alkali metal carbonates as disclosed in German Patent Application No. 2,321,001 published on Nov. 15, 1973.

Aluminosilicate builders are especially useful in the present invention. Aluminosilicate builders are of great importance in most currently marketed heavy duty granular detergent compositions, and can also be a significant builder ingredient in liquid detergent formulations. Aluminosilicate builders include those having the empirical formula:

$$M_z(zAlO_2 \cdot ySiO_2)$$

wherein M is sodium, potassium, ammonium or substituted ammonium, z is from about 0.5 to about 2; and y is 1; this material having a magnesium ion exchange capacity of at least about 50 milligram equivalents of $CaCO_3$ hardness per gram of anhydrous aluminosilicate. Preferred aluminosilicates are zeolite builders which have the formula:

$$Na_z[(AlO_2)_z (SiO_2)_y] \cdot xH_2O$$

wherein z and y are integers of at least 6, the molar ratio of z to y is in the range from 1.0 to about 0.5, and x is an integer from about 15 to about 264.

Useful aluminosilicate ion exchange materials are commercially available. These aluminosilicates can be crystalline or amorphous in structure and can be naturally-occurring aluminosilicates or synthetically derived. A method for producing aluminosilicate ion exchange materials is disclosed in U.S. Pat. No. 3,985,669, Krummel, et al, issued Oct. 12, 1976. Preferred synthetic crystalline aluminosilicate ion exchange materials useful herein are available under the designations Zeolite A, Zeolite P (B), and Zeolite X. In an especially preferred embodiment, the crystalline aluminosilicate ion exchange material has the formula:

$$Na_{12}[(AlO_2)_{12}(SiO_2)_{12}] \cdot xH_2O$$

wherein x is from about 20 to about 30, especially about 27. This material is known as Zeolite A. Preferably, the aluminosilicate has a particle size of about 0.1–10 microns in diameter.

Organic detergent builders suitable for the purposes of the present invention include, but are not restricted to, a wide variety of polycarboxylate compounds. As used herein, "polycarboxylate" refers to compounds having a plurality of carboxylate groups, preferably at least 3 carboxylates. Polycarboxylate builder can generally be added to the composition in acid form, but can also be added in the form of a neutralized salt. When utilized in salt form, alkali metals, such as sodium, potassium, and lithium, or alkanolammonium salts are preferred.

Included among the polycarboxylate builders are a variety of categories of useful materials. One important category of polycarboxylate builders encompasses the ether polycarboxylates, including oxydisuccinate, as disclosed in Berg, U.S. Pat. No. 3,128,287, issued Apr. 7, 1964, and Lamberti et al, U.S. Pat. No. 3,635,830, issued Jan. 18, 1972. See also "TMS/TDS" builders of U.S. Pat. No. 4,663,071, issued to Bush et al, on May 5, 1987. Suitable ether polycarboxylates also include cyclic compounds, particularly alicyclic compounds, such as those described in U.S. Pat. Nos. 3,923,679; 3,835,163; 4,158,635; 4,120,874 and 4,102,903.

Other useful detergency builders include the ether hydroxypolycarboxylates, copolymers of maleic anhydride with ethylene or vinyl methyl ether, 1, 3, 5-trihydroxy benzene-2, 4, 6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Citrate builders, e.g., citric acid and soluble salts thereof (particularly sodium salt), are polycarboxylate builders of particular importance for heavy duty liquid detergent formulations due to their availability from renewable resources and their biodegradability. Citrates can also be used in granular compositions, especially in combination with zeolite and/or layered silicate builders.

Also suitable in the detergent compositions of the present invention are the 3,3-dicarboxy-4-oxa-1,6-hexanedioates and the related compounds disclosed in U.S. Pat. No. 4,566,984, Bush, issued Jan. 28, 1986. Useful succinic acid builders include the $C_5$–$C_{20}$ alkyl and alkenyl succinic acids and salts thereof. A particularly preferred compound of this type is dodecenylsuccinic acid. Specific examples of succinate builders include: laurylsuccinate, myristylsuccinate, palmitylsuccinate, 2-dodecenylsuccinate (preferred), 2-pentadecenylsuccinate, and the like. Laurylsuccinates are the preferred builders of this group, and are described in European Patent Application 86200690.5/0,200,263, published Nov. 5, 1986.

Other suitable polycarboxylates are disclosed in U.S. Pat. No. 4,144,226, Crutchfield et al, issued Mar. 13, 1979 and in U.S. Pat. No. 3,308,067, Diehl, issued Mar. 7, 1967. See also Diehl U.S. Pat. No. 3,723,322.

Linear fatty acids, e.g., $C_{12}$–$C_{18}$ monocarboxylic acids, can also be incorporated into the compositions alone, or in combination with the aforesaid builders, especially citrate and/or the succinate builders, to provide additional builder activity. However, such use of fatty acids will generally result in a diminution of sudsing, which should be taken into account by the formulator.

In situations where phosphorus-based builders can be used, the various alkali metal phosphates such as the well known sodium tripolyphosphates, sodium pyrophosphate and sodium orthophosphate can be used. Phosphonate builders such as ethane-1-hydroxy-1,1-diphosphonate and other known phosphonates (see, for example, U.S. Pat. Nos. 3,159,581; 3,213,030; 3,422,021; 3,400,148 and 3,422,137) can also be used.

Bleaching Compounds—Bleaching Agents and Bleach Activators—The detergent compositions herein may optionally contain bleaching agents or bleaching compositions containing a bleaching agent and one or more bleach activators. When present, bleaching agents will typically be at levels of from about 1% to about 20%, more typically from about 1% to about 10%, of the detergent composition, especially for fabric laundering. If present, the amount of bleach activators will typically be from about 0.1% to about 60%, more typically from about 0.5% to about 40% of the bleaching composition comprising the bleaching agent-plus-bleach activator.

The bleaching agents used herein can be any of the bleaching agents useful for detergent compositions in textile cleaning, hard surface cleaning, or other cleaning purposes that are now known or become known. These include oxygen bleaches as well as other bleaching agents. Perborate bleaches, e.g., sodium perborate (e.g., mono- or tetra-hydrate) can be used herein, but, under some conditions, may undesirably interact with the polyol nonionic surfactant.

One category of bleaching agent that can be used without restriction encompasses percarboxylic ("percarbonate") acid bleaching agents and salts therein. Suitable examples of this class of agents include magnesium monoperoxyphthalate hexahydrate, the magnesium salt of meta-chloro perbenzoic acid, 4-nonylamino-4-oxoperoxybutyric acid and diperoxy-dodecanedioic acid. Such bleaching agents are disclosed in U.S. Pat. No. 4,483,781, Hartman, issued Nov. 20, 1984, U.S. patent application Ser. No. 740,446, Burns et al, filed Jun. 3, 1985, European Patent Application 0,133,354, Banks et al, published Feb. 20, 1985, and U.S. Pat. No. 4,412,934, Chung et al, issued Nov. 1, 1983. Highly preferred bleaching agents also include 6-nonylamino-6-oxoperoxycaproic acid as described in U.S. Pat. No. 4,634,551, issued Jan. 6, 1987 to Burns et al.

Peroxygen bleaching agents can also be used. Suitable peroxygen bleaching compounds include sodium carbonate peroxyhydrate, sodium pyrophosphate peroxyhydrate, urea peroxyhydrate, and sodium peroxide. Persulfate bleach (e.g., OXONE, manufactured commercially by DuPont) can also be used. Various stabilizers and coatings may be used with such bleaching agents.

Mixtures of bleaching agents can also be used.

Peroxygen bleaching agents and the perborates are preferably combined with bleach activators, which lead to the in situ production in aqueous solution (i.e., during the washing process) of the peroxy acid corresponding to the bleach activator. Various nonlimiting examples of activators are disclosed in U.S. Pat. No. 4,915,854, issued Apr. 10, 1990 to Mao et al, and U.S. Pat. No. 4,412,934. The nonanoyloxybenzene sulfonate (NOBS) and tetraacetyl ethylene diamine (TAED) activators are typical, and mixtures thereof can also be used. See also U.S. Pat. No. 4,634,551 for other typical bleaches and activators useful herein.

Bleaching agents other than oxygen bleaching agents are also known in the art and can be utilized herein. One type of nonoxygen bleaching agent of particular interest includes photoactivated bleaching agents such as the sulfonated zinc and/or aluminum phthalocyanines. See U.S. Pat. No. 4,033,718, issued Jul. 5, 1977 to Holcombe et al. Typically, detergent compositions will contain about 0.025% to about 1.25%, by weight, of sulfonated zinc phthalocyanine.

Polymeric Soil Release Agent—Any polymeric soil release agent known to those skilled in the art can optionally be employed in the compositions and processes of this invention. Polymeric soil release agents are characterized by having both hydrophilic segments, to hydrophilize the surface of hydrophobic fibers, such as polyester and nylon, and hydrophobic segments, to deposit upon hydrophobic fibers and remain adhered thereto through completion of washing and rinsing cycles and, thus, serve as an anchor for the hydrophilic segments. This can enable stains occurring subsequent to treatment with the soil release agent to be more easily cleaned in later washing procedures.

The amount of mixed nonionic/anionic surfactant needed to enhance deposition will vary with the particular soil release agent chosen, the optional presence or absence of other anionic surfactants, and their type, as well as the particular nonionic/anionic chosen. Generally, compositions will comprise from about 0.01% to about 10%, by weight, of the polymeric soil release agent, typically from about 0.1% to about 5%, and from about 4% to about 50%, more typically from about 5% to about 30% of anionic surfactant. Such compositions should generally contain at least about 1%, preferably at least about 3%, by weight, of the mixed nonionic/anionic surfactant of this invention, though it is not intended to necessarily be limited thereto.

The polymeric soil release agents for which performance is enhanced herein especially include those soil release agents having: (a) one or more nonionic hydrophile components consisting essentially of (i) polyoxyethylene segments with a degree of polymerization of at least 2, or (ii) oxypropylene or polyoxypropylene segments with a degree of polymerization of from 2 to 10, wherein said hydrophile segment does not encompass any oxypropylene unit unless it is bonded to adjacent moieties at each end by ether linkages, or (iii) a mixture of oxyalkylene units comprising oxyethylene and from 1 to about 30 oxypropylene units wherein said mixture contains a sufficient amount of oxyethylene units such that the hydrophile component has hydrophilicity great enough to increase the hydrophilicity of conventional polyester synthetic fiber surfaces upon deposit of the soil release agent on such surface, said hydrophile segments preferably comprising at least about 25% oxyethylene units and more preferably, especially for such components having about 20 to 30 oxypropylene units, at least about 50% oxyethylene units; or (b) one or more hydrophobe components comprising (i) $C_3$ oxyalkylene terephthalate segments, wherein, if said hydrophobe components also comprise oxyethylene terephthalate, the ratio of oxyethylene terephthalate:$C_3$ oxyalkylene terephthalate units is about 2:1 or lower, (ii) $C_4$–$C_6$ alkylene or oxy $C_4$–$C_6$ alkylene segments, or mixtures therein, (iii) poly (vinyl ester) segments, preferably poly(vinyl acetate), having a degree of polymerization of at least 2, or (iv) $C_1$–$C_4$ alkyl ether or $C_4$ hydroxyalkyl ether substituents, or mixtures therein, wherein said substituents are present in the form of $C_1$–$C_4$ alkyl ether or $C_4$ hydroxyalkyl ether cellulose derivatives, or mixtures therein, and such cellulose derivatives are amphiphilic, whereby they have a sufficient level of $C_1$–$C_4$ alkyl ether and/or $C_4$ hydroxyalkyl ether units to deposit upon conventional polyester synthetic fiber surfaces and retain a sufficient level of hydroxyls, once adhered to such conventional synthetic fiber surface, to increase fiber surface hydrophilicity, or a combination of (a) and (b).

Typically, the polyoxyethylene segments of (a)(i) will have degree of polymerization of from 2 to about 200, although higher levels can be used, preferably from 3 to about 150, more preferably from 6 to about 100. Suitable oxy $C_4$–$C_6$ alkylene hydrophobe segments include, but are not limited to, end-caps of polymeric soil release agents such as $MO_3S(CH_2)_nOCH_2CH_2O-$, where M is sodium and n is an integer from 4–6, as disclosed in U.S. Pat. No. 4,721,580, issued Jan. 26, 1988 to Gosselink.

Polymeric soil release agents useful in the present invention also include cellulosic derivatives such as hydroxyether cellulosic polymers, copolymeric blocks of ethylene terephthalate or propylene terephthalate with polyethylene oxide or polypropylene oxide terephthalate, and the like. Such agents are commercially available and include hydroxyethers of cellulose such as METHOCEL (Dow). Cellulosic soil release agents for use herein also include those selected from the group consisting of $C_1$–$C_4$ alkyl and $C_4$ hydroxyalkyl cellulose; see U.S. Pat. No. 4,000,093, issued Dec. 28, 1976 to Nicol, et al.

Soil release agents characterized by poly(vinyl ester) hydrophobe segments include graft copolymers of poly (vinyl ester), e.g., $C_1$–$C_6$ vinyl esters, preferably poly(vinyl acetate) grafted onto polyalkylene oxide backbones, such as polyethylene oxide backbones. See European Patent Application 0 219 048, published Apr. 22, 1987 by Kud, et al. Commercially available soil release agents of this kind include the SOKALAN type of material, e.g., SOKALAN HP-22, available from BASF (West Germany).

One type of preferred soil release agent is a copolymer having random blocks of ethylene terephthalate and polyethylene oxide (PEO) terephthalate. The molecular weight of this polymeric soil release agent is in the range of from about 25,000 to about 55,000. See U.S. Pat. No. 3,959,230 to Hays, issued May 25, 1976 and U.S. Pat. No. 3,893,929 to Basadur issued Jul. 8, 1975.

Another preferred polymeric soil release agent is a polyester with repeat units of ethylene terephthalate units containing 10–15% by weight of ethylene terephthalate units together with 90–80% by weight of polyoxyethylene terephthalate units, derived from a polyoxyethylene glycol of average molecular weight 300–5,000. Examples of this polymer include the commercially available material ZELCON 5126 (from Dupont) and MILEASE T (from ICI). See also U.S. Pat. No. 4,702,857, issued Oct. 27, 1987 to Gosselink.

Another preferred polymeric soil release agent is a sulfonated product of a substantially linear ester oligomer comprised of an oligomeric ester backbone of terephthaloyl and oxyalkyleneoxy repeat units and terminal moieties covalently attached to the backbone. These soil release agents are described fully in U.S. Pat. No. 4,968,451, issued Nov. 6, 1990 to J. J. Scheibel and E. P. Gosselink.

Other suitable polymeric soil release agents include the terephthalate polyesters of U.S. Pat. No. 4,711,730, issued Dec. 8, 1987 to Gosselink et al, the anionic end-capped oligomeric esters of U.S. Pat. No. 4,721,580, issued Jan. 26, 1988 to Gosselink, and the block polyester oligomeric compounds of U.S. Pat. No. 4,702,857, issued Oct. 27, 1987 to Gosselink.

Preferred polymeric soil release agents also include the soil release agents of U.S. Pat. No. 4,877,896, issued Oct. 31, 1989 to Maldonado et al, which discloses anionic, especially sulfoaroyl, end-capped terephthalate esters.

If utilized, soil release agents will generally comprise from about 0.01% to about 10.0%, by weight, of the detergent compositions herein, typically from about 0.1% to about 5%, preferably from about 0.2% to about 3.0%.

Chelating Agents—The detergent compositions herein may also optionally contain one or more iron and/or manganese chelating agents. Such chelating agents can be selected from the group consisting of amino carboxylates, amino phosphonates, polyfunctionally-substituted aromatic chelating agents and mixtures therein, all as hereinafter defined. Without intending to be bound by theory, it is believed that the benefit of these materials is due in part to their exceptional ability to remove iron and manganese ions from washing solutions by formation of soluble chelates.

Amino carboxylates useful as optional chelating agents include ethylenediaminetetraacetates, N-hydroxyethylethylenediaminetriacetates, nitrilotriacetates, ethylenediamine tetraproprionates, triethylenetetraaminehexaacetates, diethylenetriaminepentaacetates, and ethanoldiglycines, alkali metal, ammonium, and substituted ammonium salts therein and mixtures therein.

Amino phosphonates are also suitable for use as chelating agents in the compositions of the invention when at least low levels of total phosphorus are permitted in detergent compositions, and include ethylenediaminetetrakis (methylenephosphonates), nitrilotris (methylenephosphonates) and diethylenetriaminepentakis (methylenephosphonates). Preferably, these amino phosphonates do not contain alkyl or alkenyl groups with more than about 6 carbon atoms.

Polyfunctionally-substituted aromatic chelating agents are also useful in the compositions herein. See U.S. Pat. No. 3,812,044, issued May 21, 1974, to Connor et al. Preferred compounds of this type in acid form are dihydroxydisulfobenzenes such as 1,2-dihydroxy -3,5-disulfobenzene.

A preferred biodegradable chelator for use herein is ethylenediamine disuccinate ("EDDS"), as described in U.S. Pat. No. 4,704,233, Nov. 3, 1987, to Hartman and Perkins.

If utilized, these chelating agents will generally comprise from about 0.1% to about 10% by weight of the detergent compositions herein. More preferably, if utilized, the chelating agents will comprise from about 0.1% to about 3.0% by weight of such compositions.

Clay Soil Removal/Anti-redeposition Agents—The compositions of the present invention can also optionally contain water-soluble ethoxylated amines having clay soil removal and anti-redeposition properties. Granular detergent compositions which contain these compounds typically contain from about 0.01% to about 10.0% by weight of the water-soluble ethoxylated amines; liquid detergent compositions typically contain about 0.01% to about 5%.

The most preferred soil release and anti-redeposition agent is ethoxylated tetraethylenepentamine. Exemplary ethoxylated amines are further described in U.S. Pat. No. 4,597,898, VanderMeer, issued Jul. 1, 1986. Another group of preferred clay soil removal/antiredeposition agents are the cationic compounds disclosed in European Patent Application 111,965, Oh and Gosselink, published Jun. 27, 1984. Other clay soil removal/antiredeposition agents which can be used include the ethoxylated amine polymers disclosed in European Patent Application 111,984, Gosselink, published Jun. 27, 1984; the zwitterionic polymers disclosed in European Patent Application 112,592, Gosselink, published Jul. 4, 1984; and the amine oxides disclosed in U.S. Pat. No. 4,548,144, Connor, issued Oct. 22, 1985. Other clay soil removal and/or anti redeposition agents known in the art can also be utilized in the compositions herein. Another type of preferred antiredeposition agent includes the carboxy methyl cellulose (CMC) materials. These materials are well known in the art.

Polymeric Dispersing Agents—Polymeric dispersing agents can advantageously be utilized at levels from about 0.1% to about 7%, by weight, in the compositions herein. These materials can also aid in calcium and magnesium hardness control. Suitable polymeric dispersing agents include polymeric polycarboxylates and polyethylene glycols, although others known in the art can also be used. It is believed, though it is not intended to be limited by theory, that polymeric dispersing agents enhance overall detergent builder performance, when used in combination with other builders (including lower molecular weight polycarboxylates) by crystal growth inhibition, particulate soil release peptization, and antiredeposition.

Polymeric polycarboxylate materials can be prepared by polymerizing or copolymerizing suitable unsaturated monomers, preferably in their acid form. Unsaturated monomeric acids that can be polymerized to form suitable polymeric polycarboxylates include acrylic acid, maleic acid (or maleic anhydride), fumaric acid, itaconic acid, aconitic acid, mesaconic acid, citraconic acid and methylenemalonic acid. The presence in the polymeric polycarboxylates herein of monomeric segments, containing no carboxylate radicals such as vinylmethyl ether, styrene, ethylene, etc. is suitable provided that such segments do not constitute more than about 40% by weight.

Particularly suitable polymeric polycarboxylates can be derived from acrylic acid. Such acrylic acid-based polymers which are useful herein are the water-soluble salts of polymerized acrylic acid. The average molecular weight of such polymers in the acid form preferably ranges from about 2,000 to 10,000, more preferably from about 4,000 to 7,000 and most preferably from about 4,000 to 5,000. Water-soluble salts of such acrylic acid polymers can include, for example, the alkali metal, ammonium and substituted ammonium salts. Soluble polymers of this type are known materials. Use of polyacrylates of this type in detergent compositions has been disclosed, for example, in Diehl, U.S. Pat. No. 3,308,067, issued Mar. 7, 1967.

Acrylic/maleic-based copolymers may also be used as a preferred component of the dispersing/anti-redeposition agent. Such materials include the water-soluble salts of copolymers of acrylic acid and maleic acid. The average molecular weight of such copolymers in the acid form preferably ranges from about 2,000 to 100,000, more preferably from about 5,000 to 75,000, most preferably from about 7,000 to 65,000. The ratio of acrylate to maleate segments in such copolymers will generally range from about 30:1 to about 1:1, more preferably from about 10:1 to 2:1. Water-soluble salts of such acrylic acid/maleic acid copolymers can include, for example, the alkali metal, ammonium and substituted ammonium salts. Soluble acrylate/maleate copolymers of this type are known materials which are described in European Patent Application No. 66915, published Dec. 15, 1982.

Another polymeric material which can be included is polyethylene glycol (PEG). PEG can exhibit dispersing agent performance as well as act as a clay soil removal/antiredeposition agent. Typical molecular weight ranges for these purposes range from about 500 to about 100,000, preferably from about 1,000 to about 50,000, more preferably from about 1,500 to about 10,000.

Polyaspartate and polyglutamate dispersing agents may also be used, especially in conjunction with zeolite builders.

Brightener—Any optical brighteners or other brightening or whitening agents known in the art can be incorporated at levels typically from about 0.05% to about 1.2%, by weight, into the detergent compositions herein. Commercial optical brighteners which may be useful in the present invention can be classified into subgroups which include, but are not necessarily limited to, derivatives of stilbene, pyrazoline, coumarin, carboxylic acid, methinecyanines, dibenzothiphene-5,5-dioxide, azoles, 5- and 6-membered-ring heterocycles, and other miscellaneous agents. Examples of such brighteners are disclosed in "The Production and Application of Fluorescent Brightening Agents", M. Zahradnik, Published by John Wiley & Sons, New York (1982).

Specific examples of optical brighteners which are useful in the present compositions are those identified in U.S. Pat. No. 4,790,856, issued to Wixon on Dec. 13, 1988. These brighteners include the PHORWHITE series of brighteners from Verona. Other brighteners disclosed in this reference include: Tinopal UNPA, Tinopal CBS and Tinopal 5BM; available from Ciba-Geigy; Arctic White CC and Artic White CWD, available from Hilton-Davis, located in Italy; the 2-(4-styryl-phenyl)-2H- naphthol[1,2-d]-triazoles; 4,4'-bis- (1,2,3-triazol-2-yl)-stil- benes; 4,4'-bis-(styryl) bisphenyls; and the y-aminocoumarins. Specific examples of these brighteners include 4-methyl-7-diethyl- amino coumarin; 1,2-bis(-benzimidazol-2-yl)ethylene; 1,3-diphenylphrazolines; 2,5-bis(benzoxazol-2-yl)thiophene; 2-styryl-naphth-[1,2-d]oxazole; and 2-(stilbene-4-yl)-2H-naphtho- [1,2-d]triazole. See also U.S. Pat. No. 3,646,015, issued Feb. 29, 1972 to Hamilton.

In addition to the foregoing ingredients which are generally employed in fabric laundry, dishwashing and hard surface cleaners for cleansing and sanitizing purposes, the surfactant compositions herein can also be used with a variety of other adjunct ingredients which provide still other benefits in various compositions within the scope of this invention. The following illustrates a variety of such adjunct ingredients, but is not intended to be limiting therein.

Fabric Softeners—Various through-the-wash fabric softeners, especially the impalpable smectite clays of U.S. Pat. No. 4,062,647, Storm and Nirschl, issued Dec. 13, 1977, as well as other softener clays known in the art, can be used typically at levels of from about 0.5% to about 10% by weight in the present compositions to provide fabric softener benefits concurrently with fabric cleaning. The polyhydroxy fatty acid amides of the present invention cause less interference with the softening performance of the clay than do the common polyethylene oxide nonionic surfactants of the art. Clay softeners can be used in combination with amine and cationic softeners, as disclosed, for example, in U.S. Pat. No. 4,375,416, Crisp et al, Mar. 1, 1983 and U.S. Pat. No. 4,291,071, Harris et al, issued Sep. 22, 1981.

Hair Care Ingredients—Shampoo compositions formulated in the manner of this invention can contain from about 0.05% to about .10% by weight of various agents such as: conditioners, e.g., silicones (see, for example, U.S. Pat. Nos. 4,152,416 and 4,364,847); antidandruff agents such as the pyridinethiones, especially zinc pyridinethione (see U.S. Pat. Nos. 4,379,753 and 4,345,080), selenium compounds such as selenium sulfide and OCTOPIROX; hair styling polymers (see U.S. Pat. Nos. 4,012,501 and 4,272,511); and pediculicides (anti-lice agents) such as LINDANE and various pyrethrins (see British Patent 1,593,601 and U.S. Pat. No. 4,668,666).

Other Ingredients—A wide variety of other ingredients useful in detergent compositions can be included in the compositions herein, including other active ingredients, carriers, hydrotropes, processing aids, dyes or pigments, solvents for liquid formulations, etc.

Liquid detergent compositions can contain water and other solvents as carriers. Low molecular weight primary or secondary alcohols exemplified by methanol, ethanol, propanol, and isopropanol are suitable. Monohydric alcohols are preferred for solubilizing surfactant, but polyols such as those containing from 2 to about 6 carbon atoms and from 2 to about 6 hydroxy groups (e.g., 1,3-propanediol, ethylene glycol, glycerine, and 1,2-propanediol) can also be used.

Thickeners can optionally be added to control product viscosity. Typical thickeners include but are not limited to methyl cellulose ethers, hydroxy ethyl cellulose and derivatives thereof, gums, sugars, polysaccharides, polycarboxylate, polyacrylic acid, polyethylene glycol, polyquaternium, etc. Polyquaterniums, e.g. Quatrisoft LM200™ are preferred in certain formulas of the present invention (i.e. 2-butyl-1-octanoic acid containing compositions.

Formulations—The formulation of effective, modern detergent compositions poses a considerable challenge, especially in the absence of phosphate builders. For fabric laundering, the formulator is required to address the removal of a wide variety of soils and stains, many of which are termed "greasy/oily" soils, such as foods, cosmetics, motor oil, and the like, from a wide variety of fabric surfaces and under a spectrum of usage conditions, ranging from boil wash temperatures preferred by some users to laundering temperatures as cold as 5° C. preferred by others. Local factors, especially water hardness levels and the presence or absence of metal cations such as iron in local wash water supplies, can dramatically impact detergency performance. Like-wise, the formulator of hand dishwashing compositions must provide compositions which remove high loads of greasy food residues, but which do so under conditions which are not irritating to the user's skin nor damaging to the articles being washed. It is especially difficult to provide good grease removal at near-neutral pH's.

It will be appreciated by the formulators of detergent compositions that, at sufficiently low interfacial tensions, it is theoretically possible to provide what might be termed "spontaneous emulsification" of greasy/oily soil. If such spontaneous emulsification were to be secured, it would very considerably enhance grease/oil removal from substrates such as fabrics, dishware, environmental hard surfaces, and the like. While extremely low interfacial tensions and, presumably, spontaneous emulsification, have possibly been achievable with specialized surfactants such as the fluorinated surfactants known in the art, the present invention provides a new, mild surfactant system to achieve this desirable result. Moreover, spontaneous emulsification may be achievable with some specialized surfactants only at relatively high pH's is in the range of 10–11, whereas this desirable result is also achievable with the present compositions even in the near-neutral pH range of about 6.5–9. This is particularly important for hand-washing operations, for example, hand dishwashing, where skin mildness is of concern to the user.

While the polyhydroxy fatty acid amides employed in the practice of this invention are, structurally, nonionic-type surfactants, it has now surprisingly been discovered that the conformation of polyhydroxy fatty acid amides may be changed due to interaction between water hardness ions, especially calcium cations and the specially selected soaps or anionic surfactant. This may increase the packing of the polyhydroxy fatty acid amides at the oil/water interface. Whatever the explanation at the molecular level, the net results are the lower interfacial tensions and improved cleaning benefits which are associated with the compositions of this invention, especially with respect to the removal of greasy/oily soils.

Somewhat surprisingly, it has further been determined that no particular interaction seems to occur solely in the presence of magnesium ions. This is not to say, however, that magnesium ions are not useful in the present compositions. To the contrary, it has now also been determined that, while the presence of calcium ions improves the grease/oil removal performance of the compositions, the presence of magnesium ions provides increased suds levels. Inasmuch as most consumers have come to expect high suds levels in hand-wash products, especially hand dishwashing compositions, the formulator may advantageously employ both calcium and magnesium ions in such compositions to provide dual cleaning/sudsing benefits.

It will further be appreciated that, while the calcium and/or optional magnesium ions may be incorporated into the compositions herein, the formulator may determine that it can be acceptable practice to rely on natural water hardness to provide such ions to the compositions under in-use situations. This may be a reasonable expedient, since as little as 2 gr/gal calcium hardness can provide substantial benefits. However, the formulator will most likely decide to add the calcium and/or optional magnesium ions directly to the compositions, thereby assuring their presence in the in-use situation. Under such circumstances, and especially when formulating liquid products wherein the presence of precipitates may be undesirable, it may be preferred to add the calcium and/or magnesium to the compositions in the form of a lightly complexed chelate, such as calcium malate or maleate, magnesium malate or maleate, or the like, all as noted hereinabove.

The detergent compositions herein will preferably be formulated such that during use in aqueous cleaning operations, the wash water will have a pH of between about 6.5 and about 11, preferably between about 7.0 and about 10.5. Liquid product formulations preferably have a pH between about 7.5 and about 9.5, more preferably between about 7.5 and about 8.5. Techniques for controlling pH at recommended usage levels include the use of buffers, alkalis, acids, etc., and are well known to those skilled in the art.

The following are typical, nonlimiting examples which illustrate the use of the mixed nonionic/anionic/special soap systems provided by this invention to prepare fully-formulated detergent compositions. In general, such compositions used in the cleaning methods of this invention will provide superior emulsification, and even spontaneous emulsification, of grease/oil under conventional usage conditions in aqueous media at usage levels of about 200 ppm, preferably about 600 ppm, and higher.

EXAMPLE I

A liquid laundry detergent composition herein comprises the following.

| Ingredient | % (wt.) |
| --- | --- |
| Nonionic/anionic* | 15.0 |
| 2-butyl-octanoic acid | 5.0 |
| Sodium citrate | 1.0 |
| $C_{10}$ alcohol ethoxylate (3) | 13.0 |
| Monoethanolamine | 2.5 |
| Water/propylene glycol/ethanol (100:1:1) | Balance |

*1:1 mixture of cocoalkyl N-methyl glucamide and its sulfated counterpart surfactant.

EXAMPLE II

A granular detergent herein comprises the following.

| Ingredient | % (wt.) |
|---|---|
| Nonionic/anionic* | 10.0 |
| Zeolite A (1–10 micrometer) | 26.0 |
| 2-butyl octanoic acid | 4.0 |
| $C_{12-14}$ alkyl sulfate, Na salt | 5.0 |
| Sodium citrate | 5.0 |
| Sodium carbonate | 20.0 |
| Optical brightener | 0.1 |
| Detersive enzyme** | 1.0 |
| Sodium sulfate | 15.0 |

*1:1 mixture of tallow alkyl N-methyl glucamide and its sulfated counterpart surfactant, Na salt.
**Lipolytic enzyme preparation (LIPOLASE).

EXAMPLE III

The compositions of Example I and II are modified by including 0.5% of a commercial proteolytic enzyme preparation (ESPERASE) therein. Optionally, 0.5% of a commercial amylase preparation (TERMAMYL), together with 0.5% of a commercial lipolytic enzyme preparation (LIPOLASE) can be co-incorporated in such liquid and solid detergent compositions.

EXAMPLE IV

A dishwashing composition with high grease removal properties is as follows.

| Ingredient | % (wt.) |
|---|---|
| $C_{12}$ N-methyl glucamide | 9.0 |
| $C_{12}$ ethoxy (1) sulfate | 12.0 |
| 2-methyl undecanoic acid | 4.5 |
| $C_{12}$ ethoxy (2) carboxylate | 4.5 |
| $C_{12}$ alcohol ethoxylate (4) | 3.0 |
| $C_{12}$ amine oxide | 3.0 |
| Sodium cumene sulfonate | 2.0 |
| Ethanol | 4.0 |
| $Mg^{++}$ (as $MgCl_2$) | 0.2 |
| $Ca^{++}$ (as $CaCl_2$) | 0.4 |
| Water | Balance |

EXAMPLE V

Light duty liquid dishwashing detergent compositions having high grease removal properties and sufficient viscosity for use as light duty liquid formulation are as follows.

| Ingredient | % (wt.) Va | Vb |
|---|---|---|
| $C_{12,13}$ ethoxy (1) sulfate | 12.00 | 10.00 |
| $C_{12,13}$ ethoxy (3) sulfate | 5.00 | 2.00 |
| $C_{12}$ N-methyl glucamide | 7.00 | 9.00 |
| $C_{12,13}$ ethoxy (3) carboxylate | 4.00 | 0.00 |
| special secondary soap[1] | 4.00 | 4.50 |
| $C_{11}$ alcohol ethoxylate (9) | 3.00 | 4.50 |
| $C_{12-14}$ dimethyl amine oxide | 1.00 | 1.50 |
| $C_{12-16}$ dimethyl betaine | 2.00 | 2.00 |
| Sodium cumene sulfonate | 2.00 | 3.70 |
| Ethanol | 2.00 | 2.00 |
| $Ca^{++}$ | 0.18 | 0.18 |
| $Mg^{++}$ | 0.60 | 0.60 |
| Thickener, e.g., Quatrisoft LM200 or | 0.10 | 0.50 |
| methyl cellulose ether | | |
| Water, trim | balance | balance |

[1]2-butyl octanoic acid or any mixture of 2-methyl dodecanoic acid, 2-ethyl undecanoic acid, 2-propyl decanoic acid, 2-butyl nonanoic acid, 2-pentyl octanoic acid

EXAMPLE VI

Light duty liquid dishwashing detergent compositiong having good grease removal and acceptable product odor are as follows.

| Ingredient | % (wt. %) | |
|---|---|---|
| $C_{12,13}$ ethoxy (1) sulfate, sodium | 12.00 | 10.00 |
| $C_{12,13}$ ethoxy (3) sulfate, sodium | 5.00 | 2.00 |
| $C_{12}$ N-methyl glucamide | 7.00 | 9.00 |
| Propylene glycol | 0.64 | 0.82 |
| $C_{12,13}$ ethoxy (3) carboxylate | 4.00 | 0.00 |
| 2-butyl octanoic acid | 4.00 | 4.50 |
| $C_{11}$ alcohol ethoxylate (9) | 3.00 | 4.50 |
| $C_{12-14}$ dimethyl amine oxide | 1.00 | 1.50 |
| $C_{12-16}$ dimethyl betaine | 2.00 | 2.00 |
| Sodium cumene sulfonate | 2.00 | 3.70 |
| Ethanol | 1.00 | 1.00 |
| $Ca^{++}$ (as Ca formate) | 0.18 | 0.18 |
| $Mg^{++}$ (as $MgCl_2$) | 0.60 | 0.60 |
| Diethylenetriamine penta acetic acid | 0.06 | 0.06 |
| Perfume | 0.15 | 0.15 |
| Water, trim | balance | balance |

EXAMPLE VII

A shampoo composition is prepared according to Example IV by deleting the magnesium ions.

EXAMPLE VIII

The composition of Example II is provided in the form of a bar, which is useful in hand fabric laundering operations of the type which are conducted in those geographies where machine fabric laundering is sparsely used.

EXAMPLE IX

The granular compositions hereinabove are modified by the addition of a bleaching amount of a mixture of sodium perborate and NOBS to provide a fabric bleaching function.

What is claimed is:

1. A liquid detergent composition comprising from about 25% to 65% by weight of a mixed nonionic/anionic soap surfactant system which comprises:

a) a polyhydroxy fatty acid amide of the formula

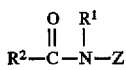

wherein $R^1$ is H, $C_1$–$C_8$ hydrocarbyl, 2-hydroxyethyl, 2-hydroxypropyl, or a mixture thereof, $R^2$ is $C_5$–$C_{32}$ hydrocarbyl, and Z is a polyhydroxyhydrocarbyl moiety having a linear hydrocarbyl chain with at least two hydroxyls directly connected to the chain; and b) an anionic surfactant which is a member or mixtures thereof selected from the group consisting of primary and secondary alkyl and alkenyl sulfates, α-sulfonated fatty acid methyl esters, alkyl benzene sulfonates, alkyl ethoxy sulfates, alkyl ethoxy carboxylates, and sulfated polyhydroxy fatty acid amides, at a weight ratio of (a):(b) of from about 10:1 to about 1:10; and c) as a replacement for conventional soap material, secondary $C_{11}$–$C_{13}$ soap material selected from the group consisting of water-soluble salts of 2-methyl-1-undecanoic acid, 2-ethyl-1-decanoic acid, 2-propyl-1-nonanoic acid, 2-butyl-1-octanoic acid, 2-pentyl-1-heptanoic acid, 2-methyl-1-dodecanoic acid, 2-ethyl-1-undecanoic acid, 2-propyl-1-decanoic acid, 2-butyl-1-nonanoic acid, 2-pentyl-1-octanoic acid and mixtures thereof;

wherein said detergent composition is in a liquid state.

2. A composition according to claim 1 which additionally comprises up to about 3% of a source of calcium ions, a source of magnesium ions, or mixtures thereof.

3. A composition according to claim 1 wherein the anionic surfactant is an alkyl ethoxy carboxylate or sulfated polyhydroxy fatty acid amide.

4. A composition according to claim 1 which additionally contains from about 2% to about 40% by weight of an additional detersive surfactant.

5. A composition according to claim 4 wherein the additional surfactant comprises an alkoxylated alcohol or alkoxylated alkyl phenol.

6. A composition according to claim 5 wherein the additional surfactant is $C_8$–$C_{14}$ alcohol ethoxylates, the ethoxylate having from about 6 to about 12 ethoxyl groups.

7. A composition according to claim 6 wherein said soap material is selected from the group consisting of 2-butyl-1-octanoic acid, 2-pentyl-1-heptanoic, 2-propyl-1-decanoic acid, 2-butyl-1-nonanoic acid, 2-pentyl-1-octanoic acid, 2-methyl-1-dodecanoic acid, 2-ethyl-1-undecanoic acid and mixtures thereof.

* * * * *